United States Patent [19]
Yui et al.

[11] Patent Number: 4,769,500
[45] Date of Patent: Sep. 6, 1988

[54] PROCESS FOR PREPARATION OF 2,3,5-TRIMETHYLHYDROQUINONE

[75] Inventors: Tomoyuki Yui, Nagareyama; Akira Ito, Kashiwa, both of Japan

[73] Assignee: Mitsubishi Gas Chemical Company, Inc., Tokyo, Japan

[21] Appl. No.: 100,521

[22] Filed: Sep. 24, 1987

[30] Foreign Application Priority Data

Oct. 16, 1986 [JP]  Japan ................................ 61-244230

[51] Int. Cl.$^4$ ....................... C07C 37/07; C07C 37/00
[52] U.S. Cl. ..................................... 568/772; 568/766
[58] Field of Search ........................ 568/772, 766, 799

[56] References Cited

U.S. PATENT DOCUMENTS

| 2,229,573 | 1/1941 | Jung | 568/772 |
| 3,723,541 | 3/1973 | Schuster et al. | 568/772 |
| 3,839,468 | 10/1974 | Tamai et al. | 568/772 |
| 3,842,130 | 10/1974 | Kawaguchi et al. | 568/772 |
| 4,018,833 | 4/1977 | Müller et al. | 568/772 |
| 4,072,660 | 2/1978 | Müller et al. | 568/772 |

FOREIGN PATENT DOCUMENTS

| 0091937 | 6/1982 | Japan | 568/772 |
| 535279 | 1/1977 | U.S.S.R. | 568/772 |

Primary Examiner—Werren B. Lone
Attorney, Agent, or Firm—Frishauf, Holtz, Goodman & Woodward

[57] ABSTRACT

A process for preparation of 2,3,5-trimethylhydroquinone (TMHQ) from 2,3,5-trimethylbenzoquinone (TMBQ) is disclosed, comprising reducing TMBQ with hydrogen in the presence of a platinum group metal catalyst with a silica alumina support containing an alkali metal component. This process permits preparation of TMHQ of purity as high as more than 99%.

19 Claims, No Drawings

PROCESS FOR PREPARATION OF 2,3,5-TRIMETHYLHYDROQUINONE

BACKGROUND OF THE INVENTION

The present invention relates to a process for preparation of 2,3,5-trimethylhydroquinone (hereinafter referred to as "TMHQ") and more particularly to a process for preparing TMHQ from 2,3,5-trimethylbenzoquinone (hereinafter referred to as "TMBQ") through its hydrogen reduction in the presence of platinum group metals deposited on an alkali metal-containing silica alumina as a support.

TMHQ is an important material for preparation of Vitamin E ($\alpha$-tocopherol), and its demand has been rapidly increased in recent years. The quality of Vitamin E varies depending on that of TMHQ as the starting material. Thus, from a viewpoint of the quality of the product Vitamin E and also from an economic standpoint in the preparation thereof, it is required for TMHQ to have a high purity.

As is well known in the art, TMHQ can be prepared from various starting materials. Among these known methods is most predominant a method of preparing TMHQ through TMBQ.

One of the known methods to prepare TMHQ from TMBQ as the starting material is a method in which TMBQ is reduced with reducing agents such as sodium hydrogensulfite (Japanese patent application laid-open No. 108032/1974) and sulfur dioxide (Japanese patent publication No. 14455/1984). This method, however, has disadvantages in that the reducing agents are expensive, the yield is low, and impurities resulting from the reducing agent are readily incorporated in the product.

Another method is to reduce TMBQ with hydrogen in the presence of a catalyst (e.g., U.S. Pat. No. 2,229,573). This method is advantageous in that the reducing agent is inexpensive and is easy to separate because it is gas. Catalysts to be used in the method which have heretofore been known include catalysts comprising activated metals such as Raney nickel and Raney cobalt, renium, and platinum group metals such as palladium, ruthenium and rhodium as deposited on a support (Japanese Patent Publication No. 20285/1982). These catalysts can be easily separated from TMHQ and the solvent by filtration after completion of the reaction because they are solid. As described above, the hydrogenation method has advantages.

TMHQ to be used in preparation of Vitamin E which is to be utilized as a medicine or a food additive is required to have a purity as high as more than 99%. If the purity of TMHQ is lower than 99%, it is necessary to purify TMHQ. For this purification, for example, the following have been proposed: a method in which after completion of the reaction, a poor solvent is added to crystallize TMHQ from the reaction mixture (Japanese Patent Publication Nos. 26424/1976 and 20285/1982), and a method in which TMHQ once separated from the reaction mixture is recrystallized from a suitable combination of solvents (Japanese patent publication No. 20285/1982). These methods, however, have various disadvantages: for example, a large amount of solvents is used, the solvents used should be separated and recovered because they are mixed solvents, and if the purity of TMHQ is low, the amount of energy needed is increased. Moreover, as the purity of TMHQ is lower, the amount of TMHQ abondoned along with impurities is more increased, thereby leading to a reduction in the yield.

If the purity of TMHQ is sufficiently high, TMHQ can be used as the product without application of any purification operation, and even in a case where the purification is applied, the amount of energy is greatly decreased.

Thus the reaction selectivity in hydrogenation of TMBQ is a very important factor exerting great influences on the yield, purity and production cost of TMHQ, and it is of high industrial significance to develop a method whereby hydrogenation of TMBQ can be carried out with high selectivity.

In practical use of catalysts, the catalyst life is important from an economic standpoint and also from a viewpoint of operation; that is, it is essential for industrial catalysts that not only the activity and selectivity at an initial stage of use are high, but also the high activity and high selectivity are maintained over a long period of time. Also in hydrogenation catalysts for TMBQ, the catalyst life is important.

As supports for platinum metals which are to be used in hydrogenation of TMBQ, active carbon (U.S. Pat. No. 2,229,573), alumina (Japanese Patent Application Laid-Open No. 100430/1977) and silica, pumice and silicic acid (Japanese Patent Publication No. 23487/1976) are known. However, in hydrogenation of TMBQ in the presence of catalysts comprising platinum group metals deposited on the above supports, side reactions such as addition of hydrogen to carbon-carbon double bonds will occur, thereby leading to a reduction in the selectivity of the desired product TMHQ. High purification, therefore, is needed to obtain the product of high purity.

Moreover the service life of the above catalysts is not sufficiently long. Thus various attempts to lengthen the catalyst life have been made as in, for example, Japanese Patent Publication No. 42964/1979, but with no satisfactory results.

SUMMARY OF THE INVENTION

An object of the present invention is to provide a process for preparing high purity TMHQ by hydrogenation of TMBQ.

Another object of the present invention is to provide a hydrogenation method of TMBQ whereby TMHQ can be obtained with high selectivity.

Still another object of the present invention is to provide a process for preparing TMHQ by hydrogenation of TMBQ by the use of a platinum group metal catalyst.

A further object of the present invention is to provide a platinum group metal catalyst for hydrogenation of TMBQ to prepare TMHQ, which can maintain its high activity and high selectivity over a long period of time.

It has been found that the objects are attained by using platinum group metal catalysts using alkali metal-containing silica alumina as a support.

The present invention relates to a process for preparing 2,3,5-trimethylhydroquinone by hydrogenation of 2,3,5-trimethylbenzoquinone in the presence of a platinum group metal catalyst using alkali metal-containing silica alumina as a support.

DETAILED DESCRIPTION OF THE INVENTION

The process of the present invention is characterized in that in preparation of TMHQ through hydrogenation of TMBQ by the use of platinum group metals, silica alumina containing alkali metals is used as a support.

The present invention produces various advantages. For example, since the process of the present invention permits hydrogenation of TMBQ into TMHQ in high selectivity, high purity TMHQ can be easily obtained without application of any additional post-treatment.

Since the catalyst for use in the process of the present invention has a long service life, it is not necessary to exchange frequently and thus the process of the present invention can be carried out economically.

The present invention will hereinafter be explained in detail.

The ratio of silica to alumina in the support is not critical; preferably the silica/alumina ratio (weight) is from 90/10 to 40/60. Any of so-called low alumina in which the silica/alumina ratio (weight) is in the vicinity of 87/13 and so-called high alumina in which the silica/alumina ratio (weight) is in the vicinity of 75/25, which are usually in industrial use, can be used in the present invention.

Alkali metals may be contained in any form in silica alumina. Usually silica alumina containing alkali metals in the form of oxide, hydroxide, sulfate, silicate, aluminate, aluminosilicate or mixtures thereof is used.

As the alkali metals, lithium, sodium, potassium, rubisium and cesium are used alone or in combination with each other. Of these metals, sodium and potassium are preferred, with sodium being most preferred.

The alkali metal content of the silica alumina as used herein is 2 to 20% by weight and preferably 3 to 15% by weight.

The alkali metals can be incorporated in silica alumina by any desired techniques. Typical methods for preparation of alkali metal-containing silica alumina include a method in which a portion of alkali metals contained in silicates is left in the course of preparation of silica alumina, a method in which zeolite containing alkali metals is mixed to prepare silica alumina, and a method in which silica alumina is subjected to alkali treatment. In addition, these methods can be used in combination with each other.

Part of the alkali metals contained in silica alumina is sometimes lost at the step of deposition of platinum group metals thereon. Deposition is carried out, therefore, so that the alkali metals remain in a proportion of not less than 0.1% and preferably not less than 0.5%, and of not more than 2%.

For the silica alumina support, the pore volume is preferably 0.3 to 1.0 ml/g and most preferably 0.6 to 0.8 ml/g, the average pore diameter is preferably 30 to 200 Å and most preferably 60° to 150 Å, and the particle diameter is preferably 200 to 50 mμ.

Platinum group metals which can be used include palladium, platinum, ruthenium, rhodium, iridium and osmium. Of these metals, palladium, platinum, ruthenium and rhodium are preferred, with palladium and platinum being more preferred. Most preferred is palladium.

The metal component can be deposited by the usual method which permits the deposition of platinum group metals and their compounds.

In deposition, the metal component is used in a soluble form such as chlorides, anmine complex salts, acetates, and acetylacetonates. It is preferred that the metal component is used in the form of chloride. In reduction of the platinum group metal component into the metal, the usual method using reducing agents can be employed. For example, as the reducing agent, hydrogen, formalin, sodium formate, carbon monoxide and hydrazine can be used. Preferred is a hydrogen reduction method.

The amount of the platinum group metal deposited on the support is usually 0.1 to 10% by weight, preferably 0.3 to 3% by weight based on the weight of the support.

The amount of the catalyst (metal+support) used is usually 0.5 to 30% by weight, particularly preferably 1 to 10% by weight based on the weight of TMBQ.

As the reaction solvent, solvents capable of dissolving TMBQ, TMHQ and their adduct quinhydrone can be used. For example, as well as methanol and ethanol which have been believed unsuitable because they cause coloration, aliphatic alcohols such as propyl alcohol, butyl alcohol and amyl alcohol, aromatic alcohols such as benzyl alcohol, ketones such as acetone and methyl ethyl ketone, organic acids such as acetic acid and propionic acid, organic acid esters such as methyl propionate, ethyl acetate, propyl acetate and butyl acetate, ethers such as dipropyl ether and dibutyl ether, cyclic ethers such as tetrahydrofuran and dioxane, and lactones such as γ-butyrolactone can be used. These solvents can be used alone or in combination with each other. Of these solvents, alcohols, ketones, organic acid esters and ethers are preferred. From viewpoints of solubility, ease of separation and cost, alcohols are more preferred. Most preferred are methanol and ethanol.

Hydrogen to be used is not always necessary to be pure. If desired, mixed gases of hydrogen and gases inert to the reaction, such as nitrogen and carbon dioxide gas, can be used.

The hydrogen partial pressure is usually 0.01 to 20 kg/cm$^2$ and preferably 0.1 to 10 kg/cm$^2$.

The suitable reaction temperature varies depending on the vapor pressure of the solvent used; it is usually 10° to 150° C. and preferably 20° to 120° C.

The solvent is used in an amount sufficient to completely dissolve the starting material TMBQ, the product TMHQ and their adduct quinhydrone. Thus the amount of the solvent used varies depending on the type of the solvent. Usually the solvent is used in such an amount that the concentration of the starting material TMBQ is from 5 to 30% by weight.

In accordance with the present invention, TMHQ can be prepared in a purity as high as more than 99% by hydrogenation of TMBQ. Thus there can be obtained an advantage that high purity TMHQ can be easily prepared without application of any post-treatment. Another advantage of the present invention is that the catalyst as used herein possesses a long service life (catalyst life), and thus the process of the present invention is economical.

The present invention is described in greater detail with reference to the following examples.

EXAMPLE 1

Preparation of Catalyst

Silica alumina (silica/alumina ratio (weight)=87/13) was treated in a 3% by weight aqueous solution of sodium hydroxide at 80° C. for 3 hours, and then filtered and dried.

The sodium-containing silica alumina (sodium content=4%) thus obtained was impregnated with a hydrochloric acid acidic aqueous solution of palladium chloride. After removal of water by evaporation, the sodium-containing silica alumina was dried at 110° C. and then reduced with hydrogen to obtain a catalyst. The sodium content of the catalyst thus obtained was 0.9%.

Hydrogenation 1 g of the sodium-containing silica alumina with palladium deposited thereon (amount of Pd deposited: 1%), 15 g of TMBQ and 45 g of methanol were charged in a reactor and stirred at 40° C. in a hydrogen atmosphere under ordinary pressure while feeding hydrogen until the consumption of hydrogen ended. It took 26 minutes. After the reaction was completed, the catalyst was removed by filtration and methanol was distilled away, whereupon TMHQ in a white crystal form was obtained. Conversion: 100%; selectivity (as determined by gas chromatography): 99.9%.

Using the catalyst above separated, the reaction was repeated in the same manner as above. The time taken till the consumption of hydrogen ended (i.e., reaction time) was gradually lengthened as shown below.

|  | Reaction Time (min) |
| --- | --- |
| First batch | 26 |
| 20th batch | 30 |
| 40th batch | 33 |
| 60th batch | 41 |
| 80th batch | 51 |
| 100th batch | 70 |
| 120th batch | 116 |

The TMHQ selectivity at the 120th batch was 99.8%.

The above results demonstrate that the Pd/alkali metal-containing silica alumina catalyst has a long service life and its high selectivity is maintained even after repeated use.

EXAMPLE 2

On sodium-containing silica alumina (silica/alumina ratio (weight): 70/30; sodium content: 10%; pore volume: 0.7 ml/g; average pore diameter: 100 Å; 92% of particles have particle diameters falling within the range of 200 to 75 mμ), which was obtained by allowing metallic sodium to partially remain therein in the course of preparation of the silica alumina, was deposited palladium to prepare a Pd/sodium-containing silica alumina catalyst (sodium content: 0.7%; amount of Pd deposited: 1%).

With the catalyst as prepared above, hydrogenation was performed in the same manner as in Example 1 (reaction time: 26 minutes) to obtain TMHQ (selectivity: 99.9%).

The catalyst was separated from the reaction mixture, and using the catalyst thus separated, the reaction was repeated. The reaction time was gradually lengthened as shown below.

|  | Reaction Time (min) |
| --- | --- |
| First batch | 26 |
| 20th batch | 30 |
| 40th batch | 35 |
| 60th batch | 40 |
| 80th batch | 49 |
| 100th batch | 59 |
| 120th batch | 77 |
| 140th batch | 128 |

The TMHQ selectivity at the 140th batch was 99.8%.

The above results demonstrate that the Pd/alkali metal-containing silica alumina catalyst has a long service life (catalyst life) and its high selectivity is maintained even after repeated use.

EXAMPLE 3

Preparation of Catalyst

A sodium silicate solution was geled by heating and aged, and then aluminum sulfate was added thereto. This slurry was filtered to obtain a filter cake. A suspension slurry of zeolite belonging to mordenite mixed with the filter cake and spray dried to obtain sodium-containing silica alumina (sodium content: 12%). Palladium was deposted on the sodium-containing silica alumina to prepare Pd/sodium-containing silica alumina (sodium content: 1.1%, amount of Pd deposited: 1%).

Hydrogenation

With the 1% Pd/sodium-containing silica alumina catalyst as prepared above, hydrogen reduction was performed in the same manner as in Example 1 (reaction time: 27 minutes) to prepare TMHQ (selectivity: 99.9%).

The above results demonstrate that when the Pd/alkali metal-containing silica alumina is used, selectivity is high.

COMPARATIVE EXAMPLE 1

TMHQ was prepared in the same manner as in Example 1 (reaction time: 25 minutes) except that as the catalyst, 1% Pd/silica alumina (produced by Japan Engelhard Co., Ltd.: silica/alumina ratio (weight): 72/28) was used. Selectivity was 99.2%.

The 1% Pd/silica alumina catalyst was separated from the reaction mixture, and with the 1% Pd/silica alumina catalyst thus separated, the reaction was repeated. The reaction time was gradually lengthened as shown below.

|  | Reaction Time (min) |
| --- | --- |
| First batch | 25 |
| 10th batch | 36 |
| 16th batch | 50 |
| 20th batch | 67 |
| 26th batch | 137 |

The TMHQ selectivity at the 26th batch was 95.5%.

The above results demonstrate that the life of the commercially available Pd/silica alumina catalyst is short, the initial selectivity is low, and the selectivity drops after repeated use.

COMPARATIVE EXAMPLE 2

TMHQ was prepared in the same manner as in Example 1 (reaction time: 24 minutes) except that 1% Pd/alumina (produced by Japan Engelhard Co., Ltd.) was used in place of the 1% Pd/sodium-containing silica alumina catalyst. Selectivity was 97.7%.

The 1% Pd/alumina catalyst was separated, and using the 1% Pd/alumina catalyst thus separated, the reaction was repeated. The reaction time was gradually lengthened as shown below.

|  | Reaction Time (min) |
| --- | --- |
| First batch | 24 |
| 10th batch | 35 |

-continued

|  | Reaction Time (min) |
| --- | --- |
| 16th batch | 48 |
| 20th batch | 64 |
| 26th batch | 126 |

The above results demonstrate that the selectivity of the commercially available Pd/alumina catalyst is low, and the catalyst life is short.

COMPARATIVE EXAMPLE 3

TMHQ was prepared in the same manner as in Example 1 (reaction time: 20 minutes) except that 1% Pd/active carbon (produced by Japan Engelhard Co., Ltd.) was used in place of the 1% Pd/sodium-containing silica alumina catalyst. Selectivity was 98.2%.

The 1% Pd/active carbon catalyst was separated from the reaction mixture, and with the 1% Pd/active carbon catalyst thus separated, the reaction was repeated. The reaction time was gradually lengthened as shown below.

|  | Reaction Time (min) |
| --- | --- |
| First batch | 20 |
| 10th batch | 33 |
| 13th batch | 40 |
| 20th batch | 83 |
| 22th batch | 125 |

The above results demonstrate that the selectivity of the Pd/active carbon catalyst is low and the catalyst life is short.

What is claimed is:

1. A process for preparing 2,3,5-trimethylhydroquinone which comprises reducing 2,3,5-trimethylbenzoquinone with hydrogen in the presence of a platinum group metal catalyst with alkali metal-containing silica alumina as a support.

2. The process as claimed in claim 1 wherein the silica/alumina ratio (weight) is 90/1 to 40/60.

3. The process as claimed in claim 1 wherein the alkali metal is contained in the silica alumina support in a form of oxide, hydroxide, sulfate, silicate, aluminate, alumino-silicate or a mixture thereof.

4. The process as claimed in claim 1 wherein the alkali metal is selected from lithium, sodium, potassium, rubidium, cesium or mixtures thereof.

5. The process as claimed in claim 1 wherein the alkali metal is sodium or potassium.

6. The process as claimed in claim 1 wherein the alkali metal content in the catalyst is not less than 0.1% by weight.

7. The process as claimed in claim 1 wherein the silica alumina support has a pore volume of 0.3 to 1.0 ml/g.

8. The process as claimed in claim 1 wherein the silica alumina support has an average pore diameter of 30 to 200 Å.

9. The process as claimed in claim 1 wherein the silica alumina support has a particle size of 200 to 50 $\mu$.

10. The process as claimed in claim 1 wherein the platinum group metal is selected from palladium, platinum, ruthenium, rhodium, iridium and osmium.

11. The process as claimed in claim 1 wherein the platinum group metal is selected from palladium, platinum, ruthenium and rhodium.

12. The process as claimed in claim 1 wherein the platinum group metal is palladium or platinum.

13. The process as claimed in claim 1 wherein the amount of the platinum group metal deposited on the silica alumina support is 0.1 to 10% by weight based on the weight of the support.

14. The process as claimed in claim 1 wherein the amount of the catalyst (metal+support) used is 0.5 to 30% by weight based on the weight of 2,3,5-trimethylbenzoquinone.

15. The process as claimed in claim 1 wherein the hydrogenation is carried out in a solvent capable of dissolving 2,3,5-trimethylbenzoquinone, 2,3,5-trimethylhydroquinone and their adduct, quinonehydron.

16. The process as claimed in claim 15 wherein the solvent is selected from aliphatic alcohols, aromatic alcohols, ketones, organic acids, organic acid esters, ethers, cyclic ethers, lactones and mixtures thereof.

17. The process as claimed in claim 15 wherein the solvent is methanol or ethanol.

18. The process as claimed in claim 1 wherein the hydrogenation is carried out at a hydrogen partial pressure of 0.01 to 20 kg/cm$^2$.

19. The process as claimed in claim 1 wherein the hydrogenation es carried out at a temperature of 10° to 150° C.

* * * * *